United States Patent [19]

Lemaster et al.

[11] Patent Number: 4,854,172

[45] Date of Patent: Aug. 8, 1989

[54] METHOD AND APPARATUS FOR MEASUREMENT OF DENSITY PROFILES IN WOOD COMPOSITES, USING ACOUSTIC EMISSION

[75] Inventors: Richard L. Lemaster, Pinole; David A. Dornfeld, Berkeley, both of Calif.

[73] Assignee: Regents of the University of California, Berkeley, Calif.

[21] Appl. No.: 247,872

[22] Filed: Sep. 22, 1988

[51] Int. Cl.[4] .............................................. G01N 29/04
[52] U.S. Cl. ........................................ 73/587; 73/801; 73/32 A
[58] Field of Search ............... 73/587, 588, 602, 32 A, 73/783, 859, 7, 703, 801

[56] References Cited

U.S. PATENT DOCUMENTS 4,292,847 10/1981 Tait ........................................ 73/587
4,766,647 8/1988 Ackermann Jr. et al. ........... 73/703

FOREIGN PATENT DOCUMENTS

60-152951 8/1985 Japan ...................................... 73/587

Primary Examiner—Stewart J. Levy
Assistant Examiner—Louis M. Arana
Attorney, Agent, or Firm—Owen, Wickersham & Erickson

[57] ABSTRACT

Method and apparatus for evaluating the density profile of a wood-derived specimen. A sample of the material is mounted on a lathe and rotated at high speed. An acoustic emission transducer is coupled to a cutting tool, brought into contact with the specimen to produce an AE signal, as the tool is moved across the thickness of the rotating sample. The acoustic emission signal is then transformed into an electrical signal and the resultant electrical signal is amplified and transmitted to a second amplifier for further amplification and analysis of the signal.

14 Claims, 13 Drawing Sheets

METHOD AND APPARATUS FOR MEASUREMENT OF DENSITY PROFILES IN WOOD COMPOSITES, USING ACOUSTIC EMISSION

This invention relates to method and apparatus for measurement of density profiles in wood composites, using acoustic emission.

BACKGROUND OF THE INVENTION

Manufacture of wood composite board and other building materials requires the evaluation of many variables. The size of the wood fibers and particles, the resin or adhesive content, the pressure, the pressing time, the temperature, and other factors must be determined and checked in order to produce a board of consistent quality.

An accepted measure of consistency is the density profile of the board. If the density profile of a composite board with the desired strength characteristics can be reproduced, then the strength characteristics will be maintained.

Several different methods for evaluating density profiles have been used in industry and in the laboratory. The gravimetric method, in which the specimen is planed, measured, and weighed in small increments, is the most direct. The density measurements, in this case, can be evaluated approximately every 0.030 inches (0.076 cm) of thickness.

Two methods involving radiation sources have also been evaluted. One such method uses X rays to produce a photographic image of the profile of a composite wood specimen; this method allows for virtually continuous density measurements across the cross-section of the board, with correlation made with known standards. A second such method uses a gamma ray source to scan the thickness of a specimen. The transmitted radiation is then correlated to the material density, and a continuous measurement is again possible.

Of the methods mentioned and discussed above, the conventional gravimetric method for density determination is the most time-consuming and the least resolute. Although the density calculations are the most direct (weight/volume), the measurements become more difficult to obtain as the specimen is planed, because the thickness decreases. A thicker specimen would be easier to handle, but would also require more time, due to the greater number of sections that would have to be removed.

The X ray and gamma ray methods for density measurement each provide continuous profiles of the specimen, but they also require radiation sources and a greater knowledge of equipment operation by the user. These methods are faster than the gravimetric method and provide information about densities at specific points rather than averaging the densities over small sections. Both such methods claim to be nondestructive: However, this would not be the case in practical applications in industry. The samples being evaluated must be no more than 3 inches (7.62 cm) in width; so some part of the manufactured board must be cut. The operation of these densitometers not only requires training: The densitometers also incur a substantial initial cost before consistent measurements can be made.

SUMMARY OF THE INVENTION

In the present invention, acoustic emission (AE) is used to evaluate the density profile of a specimen. A circular sample of the material is mounted on a lathe and rotated at high speed. A piezoelectric transducer coupled to a cutting tool monitors the AE signal, which is produced as the tool is moved across the thickness of the rotating sample. The signal is then amplified, as by using an AET 5000 signal analyzer, and is transmitted to an IBM PC/AT for further characterization and analysis. This technique although destructive, offers an accurate and repeatable method for density profile determination without the use of radiation or the limitation of sample size.

REVIEW OF ACOUSTIC EMISSION (AE)

Acoustic emission can be defined as the stress or pressure waves generated during dynamic processes in materials. Though usually in the ultrasonic range (typically 100 kHz –1 MHz), these waves can sometimes be sensed by the unaided ear, as when timber cracks upon being loaded to near failure. The study of these waves, as related to deformation in materials, has been limited, due to their low energy levels, which require sophisticated instrumentation for detection: Improvements in electronics have made possible great advancements in this field.

The AE signal is usually detected by an instrumentation system using sensors or transducers, which, when stimulated by stress waves, transform mechanical excitations into electrical signals. These signals are then amplified and transmitted to an oscilloscope, counter, root mean square (RMS) voltmeter, recorder, or spectrum analyzer, depending on the type of analysis desired. The most common type of transducer is a piezoelectric ceramic element, such as one of lead zirconate titanate.

The greatest problem in the application of AE in process control is the analysis or interpretation of the signals. An actual AE signal is nonperiodic, contains many frequencies, and cannot be described by an explicit mathematical relationship. This calls for the use of statistical tools in analyzing AE data. Among the various methods frequently used to characterize the emission from a material are: cumulative count, count rate, RMS voltage, spectral analysis, probability density function, auto-correlation function, and amplitude distribution analysis.

The voltage, V, of the signal can be theoretically represented as an exponentially damped sinusoidal wave according to the relationship:

$$V = V_o \dot{\epsilon}^{-\beta t} \cos 2\pi F t \qquad [1]$$

where
$V_o$ = the threshold voltage
$V$ = the initial output voltage of the transducer
$\beta$ = the damping factor
$f$ = the linear frequency
$t$ = time in seconds
$\dot{\epsilon}$ = strain rate.

Figure 1:
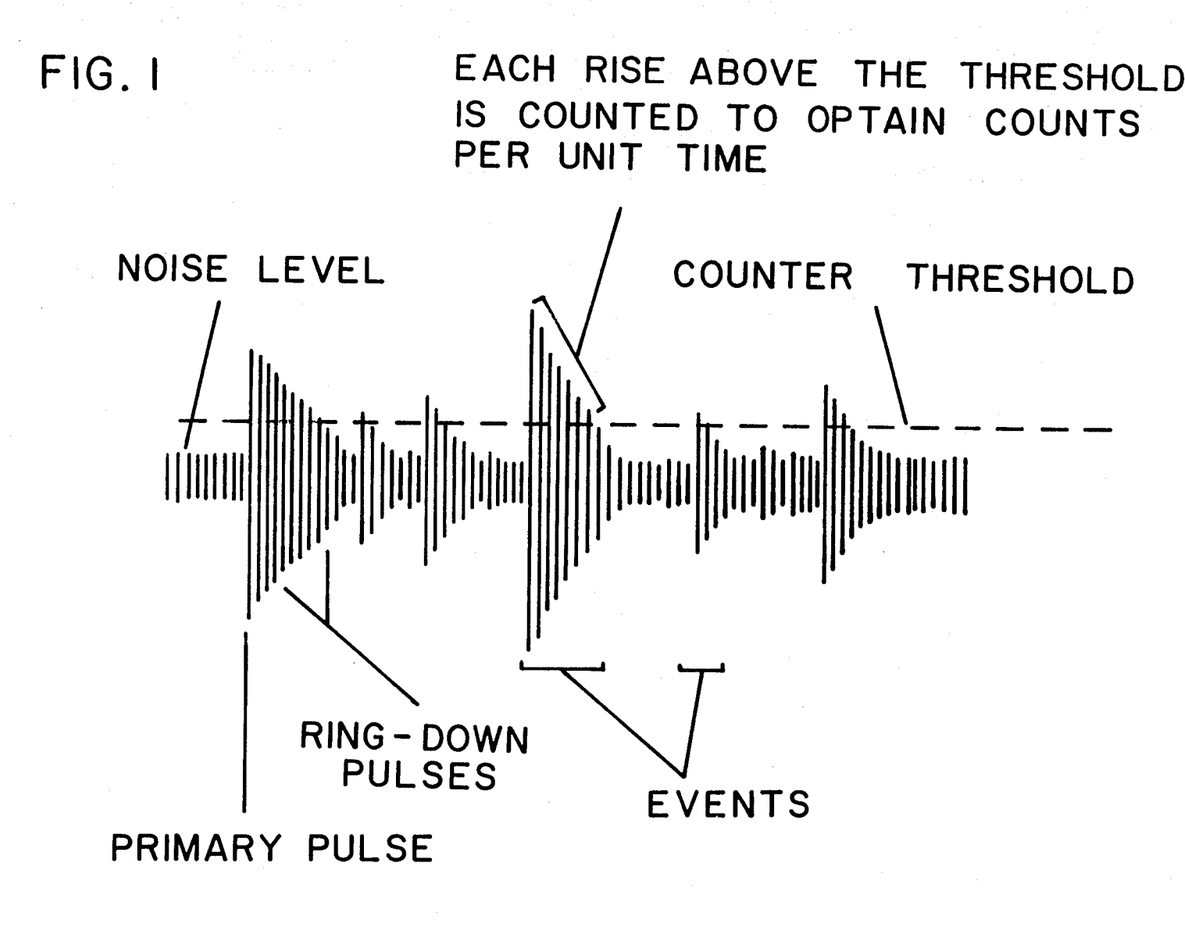
FIG. 1 is a schematic graph of an acoustic emission signal.

This V signal is due to an AE event which is defined as a single occurrence of AE activity. (See FIG. 1, below.) A sharp tap on a transducer will register one event, while a vigorous shake will register several events. The number of counts resulting from the events, is the number of times the signal caused by the events exceeded a preset threshold voltage. This means that the number of counts measured for a given event and a preset threshold voltage depends on the energy contained in the event and the damping factor $\beta$. It can be assumed that the output voltage of a transducer is proportional to the square root of the energy released during a given deformation process. This is so because the output voltage of a piezoelectric disk is proportional to the stress on the disk face and because the energy density of an elastic stress wave is proportional to the square of the stress.

The RMS voltage of a continuous AE signal can be used to measure the energy of the AE signal. Here, the term "continuous emission" (as defined by the 1964 U.S. Acoustic Emission Working Group) refers to a sustained signal level whose characteristics are such that "....the average time interval between the beginning of the emission signals of comparable amplitude is less than or comparable to the duration of the emission signals". The RMS value of the AE signal is that value of a DC signal which, if passed through the same circuit for the same time, produces the same expenditure of energy as the AE signal. Analytically, it is defined as:

$$RMS = \frac{1}{WT} \int_0^{WT} V(t) \, dt^{1/2} \quad [2]$$

where

V(t) = the function of the signal with resepct to time.
WT = the time period.

In previous studies, the inventors and others discovered that the acoustic emission was generated at the primary deformation zone at the tip of a cutting tool moving through wood. Furthermore, the levels of acoustic emission generated were found to be sensitive to the cutting parameters, such as feed speed, cutting speed and depth of cut, as well as biological factors such as density. This sensitivity of AE to density gave rise to the idea of correlating AE levels to density profiles in composite wood products.

DESCRIPTION OF SOME EMBODIMENTS OF THE INVENTION

Specimens were prepared by cutting a 15.2 cm (6 inch) diameter disk 20 from a board (not shown) of unknown density. (See FIG. 13.) The resulting circular specimen 20 was then secured to a metal face plate 22, which was mounted on a lathe 24. A disk of calibration material 19 is shown mounted on the lathe 24, although the calibration disk 19 may not be needed for every specimen 20. A piezoelectric transducer 25 (175 kHz resonant frequency) was coupled via a steel mounting bracket 26 and a resinous couplant 27 (AET-SC6) to a carbide-tipped cutting tool 28.

An AE signal 30 (See FIG. 2) received by the transducer 25 was run through a 40 dB pre-amplifier 34 and a 0.125 -2 MHz signal filter 36 to an AET 5000 Signal Analyzer 37. The transducer 25 may be mounted directly to a blade 35 on the bracket 26, as by using a clamp, if needed. A listing of the initial parameter settings can be seen in Table 1.

Figure 2:
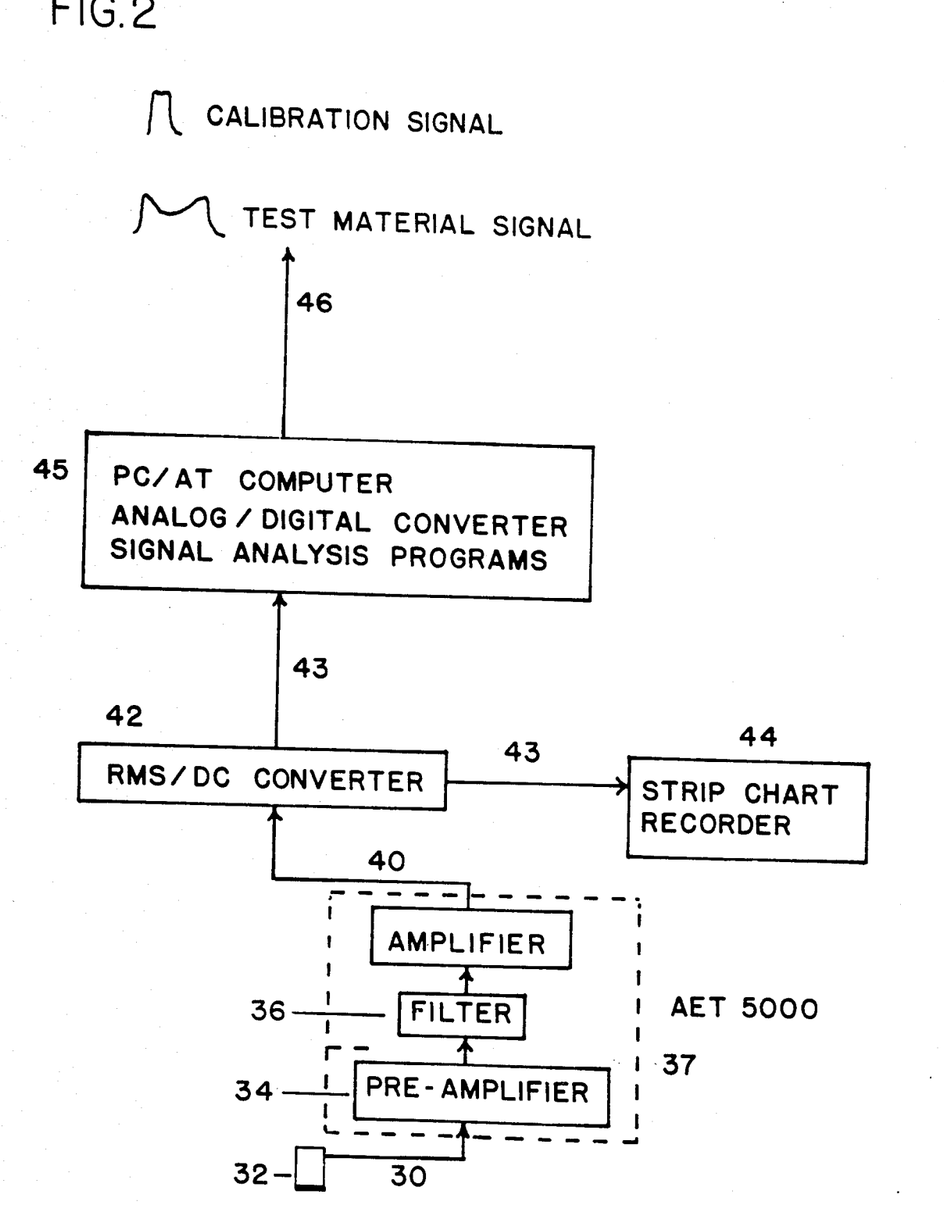
FIG. 2 is a flow sheet for simplified equipment for practicing the invention.
Figure 13:
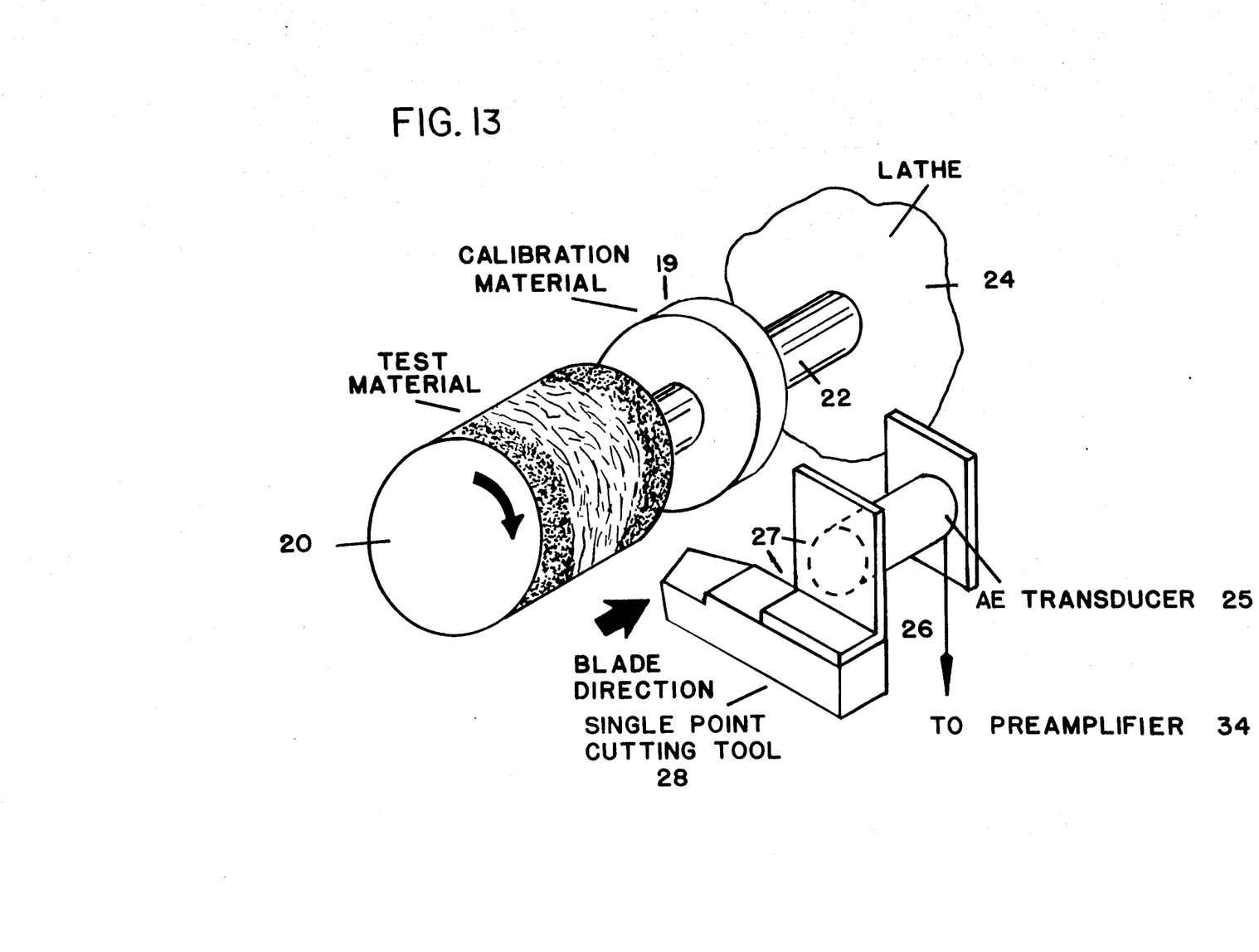
FIG. 13 is an isometric view of a lathe set-up for use in the invention, representing simple equipment for practicing the invention.

A cutting tool 28 may be of steel or ceramic or of diamond, it may be carbide tipped steel. The transducer may be quartz, lead zirconate titanate, or polyvinylidene fluoride, for example, or of other suitable material.

TABLE 1

| Initial Conditions for Experiment | |
|---|---|
| Lathe: | |
| Rotation of sample | 333 rpm |
| Feed rate of sample | 0.0064 cm/rev (0.0025 in/rev) |
| Depth of cut | ⁻0.064 cm (0.025 inch) |
| Cutting tool | Carbide single-point tool with a rake, clearance and side cutting edge angle of 5° |
| Acoustic Emission Equipment: | |
| Transducer | AET 175 KHz |
| Pre-Amplifier | AET 40dB |
| Amplifier | AET 5000 |
| Total Gain: | 72db |

The AET 5000 Signal Analyzer 37 was used to record the output signal voltage along with many other parameters, including signal rise time, ringdown counts, and peak amplitude. This was useful in checking to see whether any other signal characteristic could be used to predict material density.

The amplified signal 40 was then input to an RMS voltage converter 42. The resulting RMS voltage signal 43 was printed out on a high speed strip chart recorder 44 and was digitized into an IBM PC/AT 45 for storage and further analysis, FIG. 2 is a flow sheet of a simplified set-up.

For this setup 46, the RMS voltage was used as a comparative measure for material density evaluation. The equation:

$$RMS \text{ voltage} = f(\dot{\epsilon}, \text{volume}, \text{material property})$$

$$V = V_0 \dot{\epsilon}^{-\beta t} \cos 2\pi f t \quad [1]$$

where $V_o$ = the threshold voltage
$V$ = the initial output voltage of the transducer
$\beta$ = the damping factor
$f$ = the linear frequencey
$t$ = time in seconds
$\dot{\epsilon}$ = strain rate was used to relate RMS voltage to known quantities of the setup 46. In this setup, $\dot{\epsilon}$, the material strain rate (dependent on cutting velocity), remained constant for a given composite wood sample.

The volume of material cut, as determined by feed speed and depth of cut, was also constant for each data acquisition run. The material property of the composite specimen which varies the most is the density. For this experiment therefore, the material property related to the output RMS voltage was density. The above equation can then be simplified to:

$$RMS \text{ voltage} = (C)(\text{Density})$$

$$RMS = \frac{1}{WT} \int_0^{WT} V(t)\, dt^{1/2} \qquad [2]$$

where
$V(t)$ = the function of the signal with respect to time
$WT$ = the time period where C is a proportionally constant dependent on other aspects of the material being tested and the initial conditions for the data run. Changing such parameters as depth of cut, output signal gain, or frequency of the transducer did affect the magnitude of the RMS voltage, but the effect was constant throughout the data run (as predicted by Eq. (1) for depth of cut, for example) and thus could be incorporated into C. From this equation, absolute densities within a sample were predicted, using the output signal RMS voltage.

Since absolute densities are not normally required in a quality control application, the repeatability of the output signal voltage produced by testing a specimen allows for a sample to be checked for signal variance from a desired standard, without performing the calculations for absolute densities.

The tests for repeatability of output signal voltage involved data acquisition for different materials over three or more sequential runs. Both single density and multiple density materials were tested for consistency of output signal produced over the course of the data runs.

Once the repeatability of this method was verified, a calibration technique was used to enable the prediction of actual density profiles in the composite wood specimens tested. For a given data acquisition run, the ratio of RMS voltage to density was constant (Eq. (2)). Since this ratio was known for the calibration material, Eq. (2) was used to predict the density profile of the composite specimen by an analysis of the output RMS voltage signal.

RESULTS AND DISCUSSION
—REPEATABILITY TESTS

Figure 3:
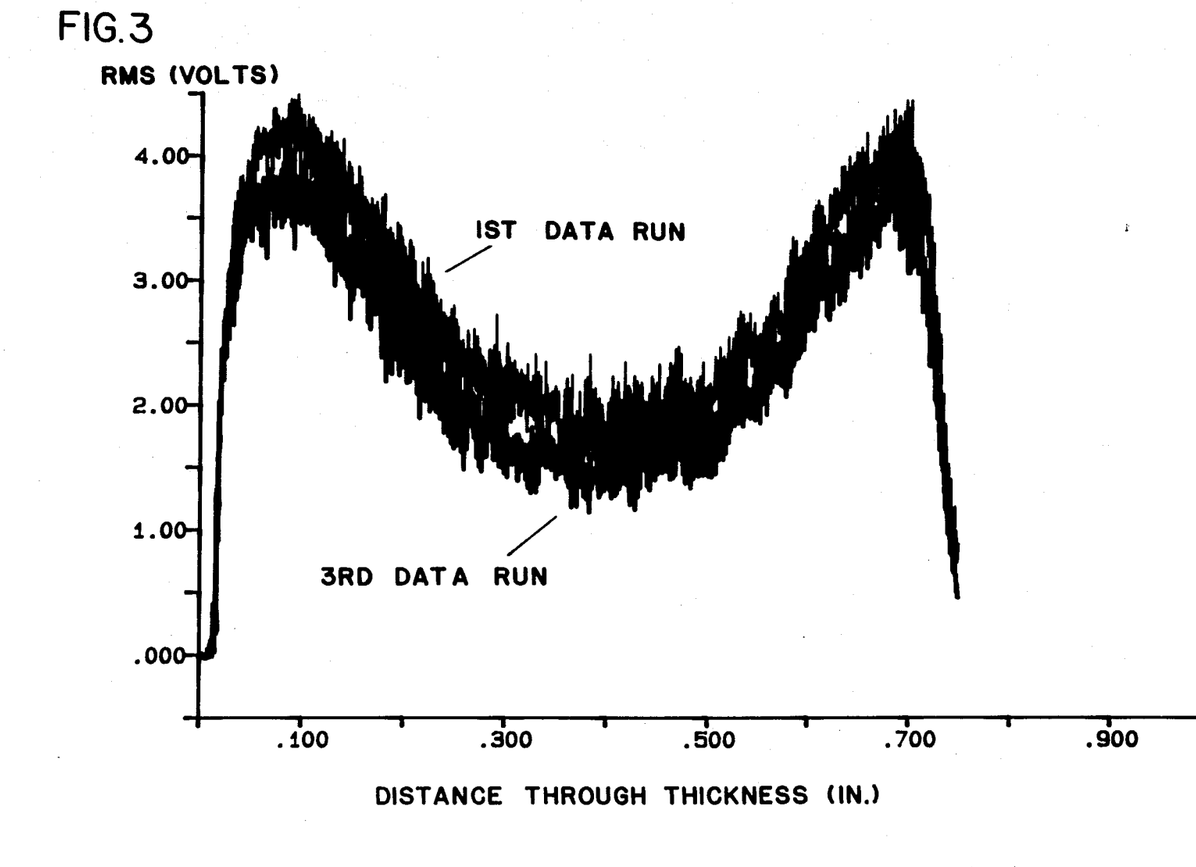
FIG. 3 is a graph of the repeatability of the technique, the test material being a high-density particle board.

A first phase considered the repeatability of the output signals produced when different materials were tested. The materials evaluated were medium-density fiberboard, and medium, to high-density particle board, and plywood, as well as materials whose density is essentially constant across the thickness, such as hardboard and solid pine (*Pinus ponderosa*). The repeatability of this density measurement technique was determined by making three separate data acquisition runs for each sample and comparing the shape and magnitudes of the output RMS signals for each run. As can be seen from FIG. 3, the shape of the output signal for high-density particle board was maintained, although the magnitudes decreased. The reduction of RMS voltage was principally due to the decreasing radius of the sample, hence reduced cutting speed or strain rate (Eq. (1)). Tool wear would also result in a decrease in the RMS levels.

Figure 4:
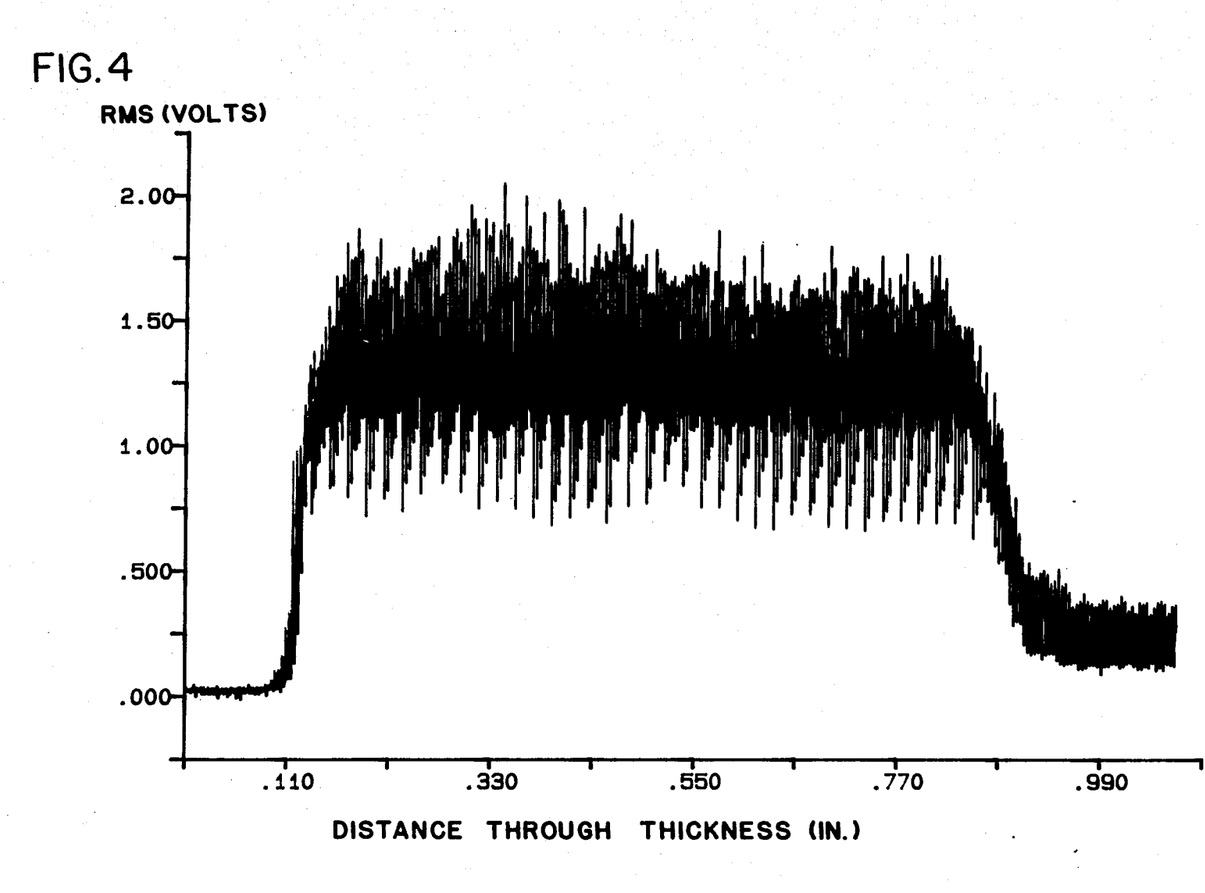
FIG. 4 is a chart of the RMS output for a solid pine sample.
Figure 5:
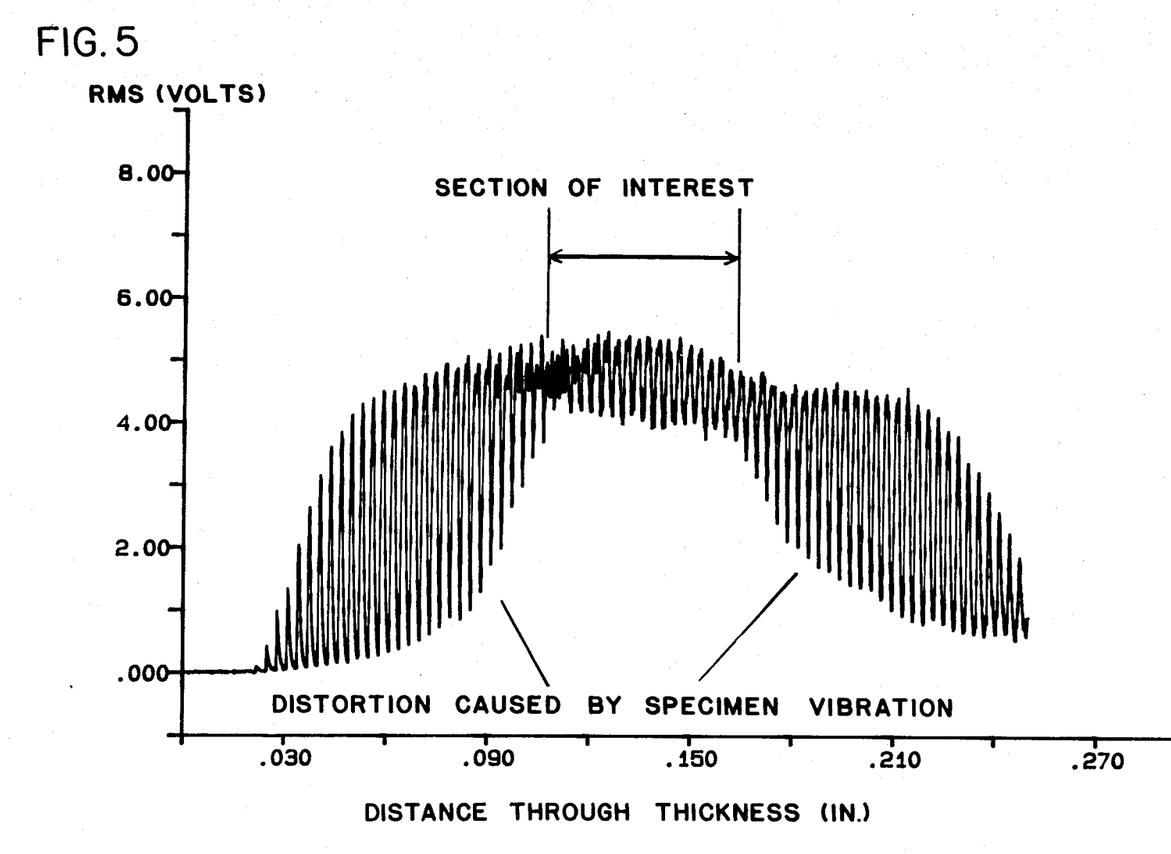
FIG. 5 is a similar chart of the RMS output for a hardboard sample.

The single density samples were run to determine whether a constant RMS voltage would be produced. Large variations in output signal for the pine sample (FIG. 4) were due to the grain of the material, in which cross-grain cutting produced a higher output signal. The average signal however, was very consistent. The same was true for the 0.635 cm (0.25 inch) thick hardboard (FIG. 5). The signal variations for this sample were due to vibrations caused by the cutting tool entering and leaving the thin and flexible specimen. The signal stabilized only after the cutting tool had moved sufficiently into the specimen to stop the vibrations of the disk. Since both samples gave consistent results over an interval, the possibility of developing a calibration technique for determining absolute densities became reasonable. This technique allows for densities of unkown samples to be calculated, based on the magnitude of the output signal produced by the single density calibration material. This eliminates variability in the testing procedure, caused by variability in the cutting speed, feed speed, cutting depth, and tool sharpness, since each run is essentially self-calibrating.

DENSITY CALIBRATION TESTS

A calibration material my be used as a reference to predict actual density profiles of different composite samples. Predicted values have been compared to actual densities as calculated by a conventional gravimetric method. In this method a sample of material is weighed and measured; a small layer is shaved off, and then reweighed and measured to get a profile. Layers of 0.064 cm (0.025 inch) in thickness are shaved; this is a finer resolution than typical methods used in industry. One method that can be adopted calls for mounting a circular sample of the test specimen on a face plate on an engine lathe and securing it in place with a bolt through the center of the sample. The sample is weighed, and a face cut made from the outside diameter of the sample to just outside the diameter of the mounting bolt. The procedure of alternately weighing and face cutting the sample may be continued for the entire thickness of the sample. This procedure appears to be superior to the planing, sawing, or sanding methods used in the past, due to the precision of the engine lathe.

Although great care was taken to maintain a high level of consistency during these measurements, the resulting densities which were calculated often fluctuated from measurement to measurement. This may be due to the extremely small amount of material being removed, which caused small deviations in measurements to be magnified when densities were calculated, as well as to actual inboard density variations. The lathe version of the gravimetric method also appeared to require a certain amount of expertise by the operator on the engine lathe. This was apparent in a visual inspection of the gravimetric samples, where some of the earlier samples exhibited evidence of fiber tear out and an uneven stopping point for subsequent cuts. This gravimetric method required approximately two hours to evaluate completely a 1.91 cm (0.75 inch) thick sample.

In calibrations, specimens from the same boards as were used for the gravimetric method were then tested by a calibration technique. Hardboard was chosen as the calibration material because of its essentially consistent through-thickness density. Almost any material, such as brass or Plexiglas may be used for calibration, as long as the actual density of the material is known. Both tempered and untempered hardboards have been used as calibration materials with no noticeable difference in results.

Figure 6:
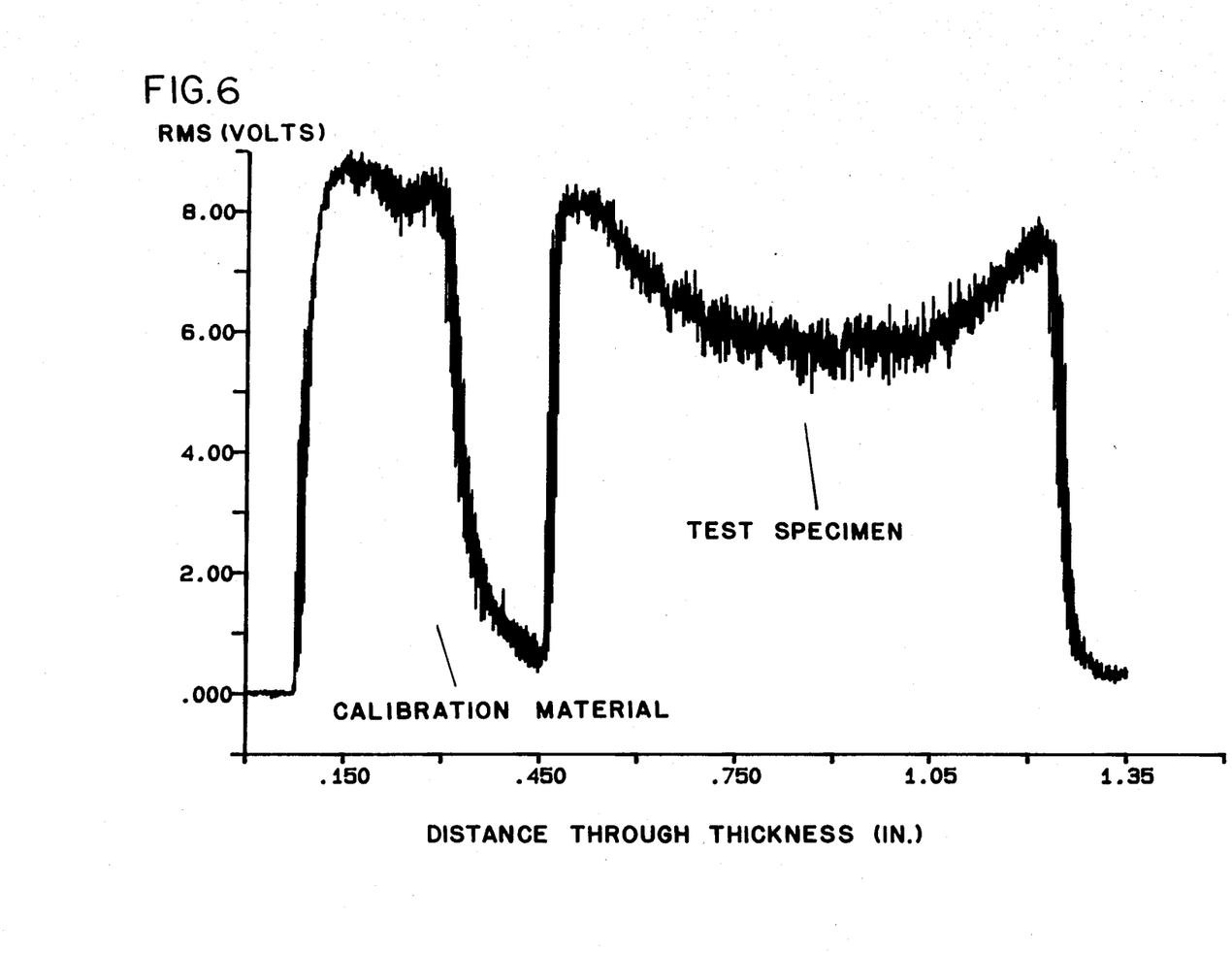
FIG. 6 is an RMS output graph for high-density particle board.

The materials evaluated, using this method, include a high-density particle board (720 kg/m$^3$ or 65 lb/ft$^3$ and a medium-density fiberboard. The unknown specimen was mounted on the lathe with the hardboard. A rubber washer separated the two specimens (FIGS. 2 and 13). The cutting tool was fed across the hardboard and then the unknown composite sample, resulting in an output signal such as shown in Fig. 6 (high-density particle board). Other signal characteristics such as rise time, ringdown counts, and peak amplitude were plotted, using the AET 5000 to see whether results similar to the voltage plots could be achieved. However, no other characteristics gave as meaningful results; so RMS voltage is preferably used throughout the remainder of the calibration.

Figure 7:
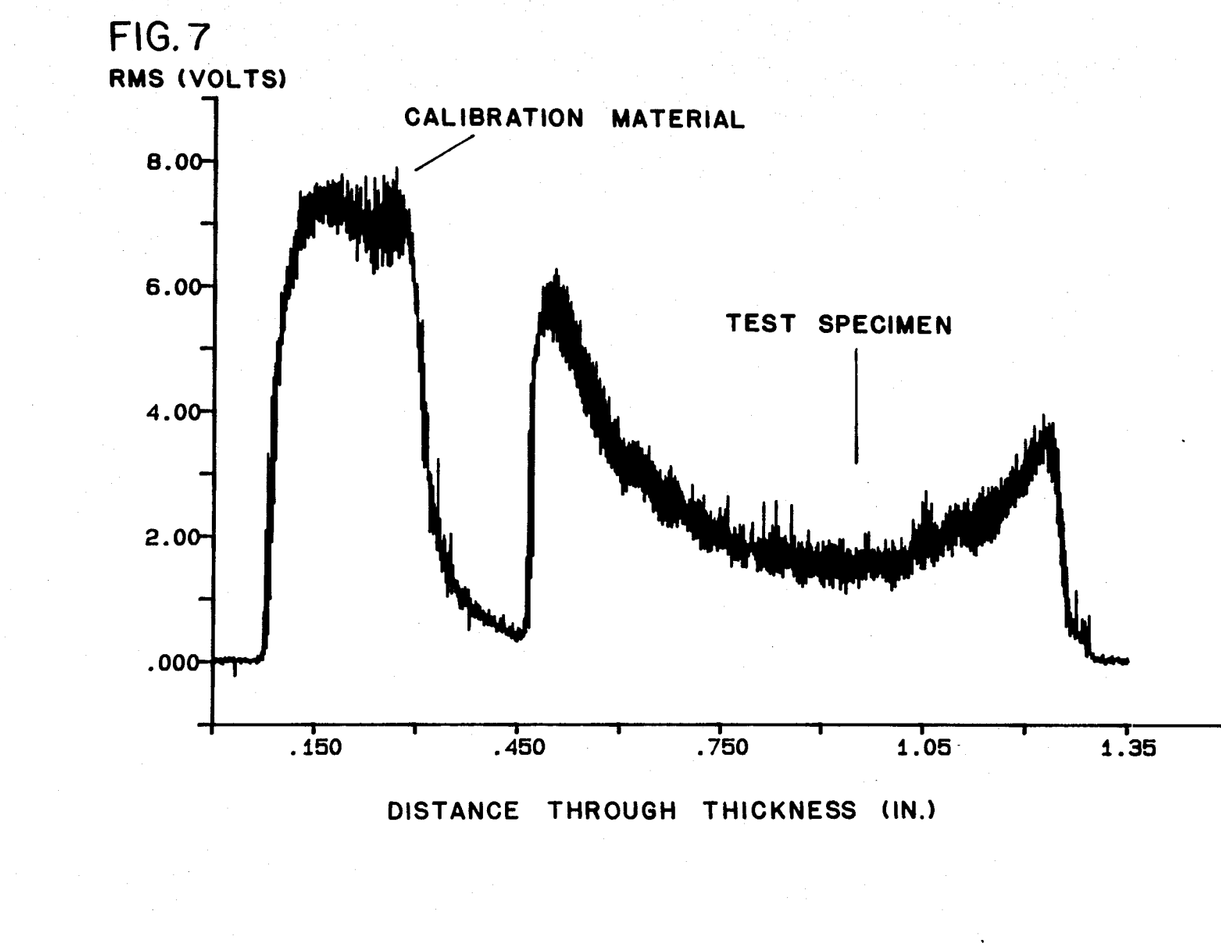
FIG. 7 is an RMS output graph for medium-density fiberboard.

A similar test specimen of medium-density fiberboard was tested next. The decreased RMS signal towards the end of the plot in FIG. 7 was due to fiber tear-out, while the blade was leaving the cut. This problem has been frequently encountered, but it is believed it can be compensated for by making subsequent cuts in the specimen from opposite sides and by adding the signals together.

Another way of reducing or eliminating the occurrence of tear-out is to use a lathe with a faster cutting speed. The 333 rpm used in a study is actually too slow to yield smooth cuts in wood.

Predicted densities have been calculated from the acquired data and compared to the results of the gravimetric method. Using a signal processing program, the output RMS voltage signal was analyzed. The amplitude of the calibration material signal was first averaged over the entire thickness, and an average RMS voltage for the hardboard was recorded. The signal produced by the unkown composite was then segmented into corresponding 0.064 (0.025 inch) intervals. The average RMS voltage for the interval was calculated and recorded over the entire thickness of the composite sample. The predicted densities were then calculated using the relationship:

$$\frac{\text{calibration density}}{\text{average } RMS \text{ voltage}} = \frac{\text{unknown density}}{\text{average interval } RMS \text{ voltage}} \quad (3)$$

A density profile was then generated, using the same interval size as the gravimetric method.

Figure 8:
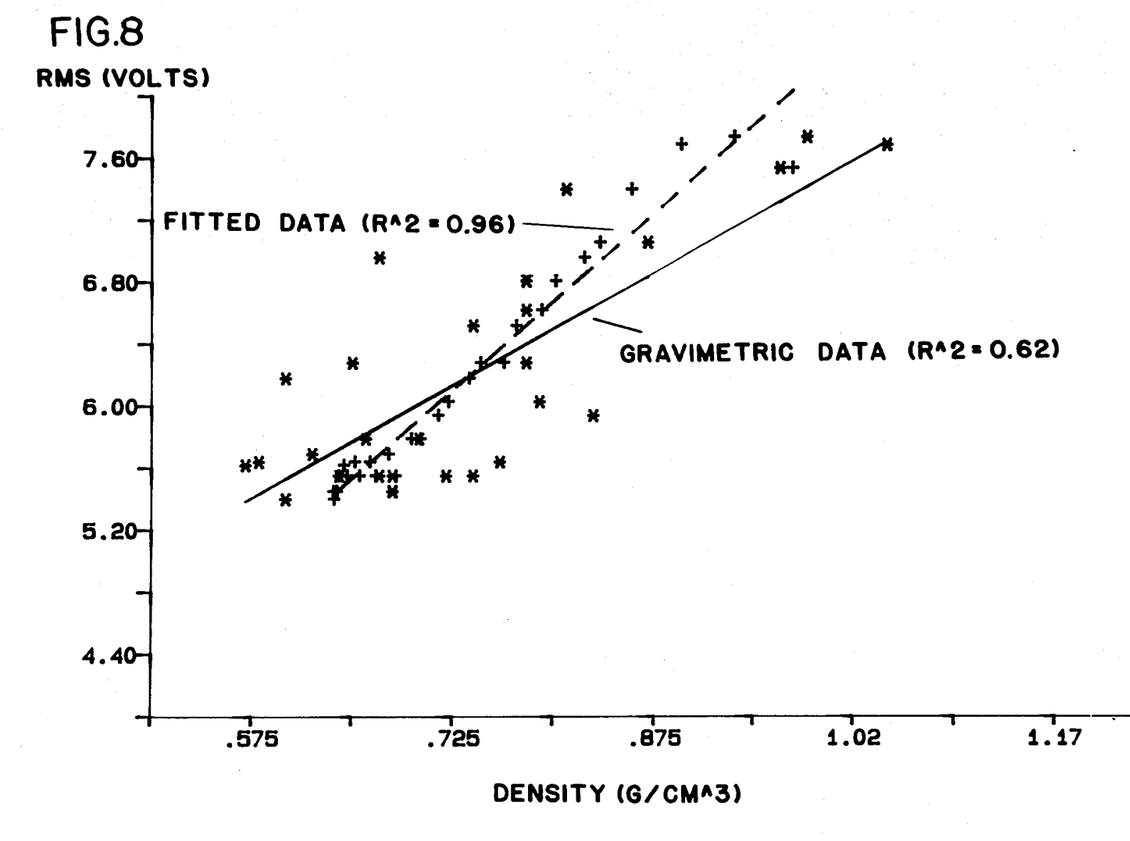
FIG. 8 is a graph of RMS versus gravimetric density for high-density particle board.

The two sets of results were compared and evaluated to determine whether the method was consistent for different materials and also for successive data runs. FIG. 8 is a graph of RMS versus the gravimetric-based density for the high-density particle board sample.

Figure 9A:
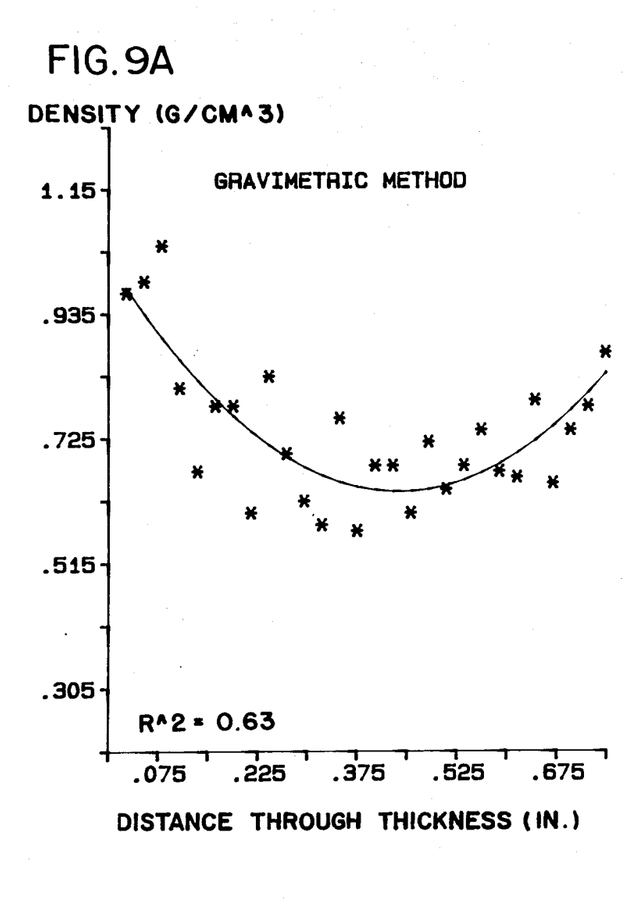
FIG. 9A and 9B hereinafter refered collectively as FIG. 9, is a graph of gravimetric and AE determined density profiles for high-density particle board.
Figure 9B:
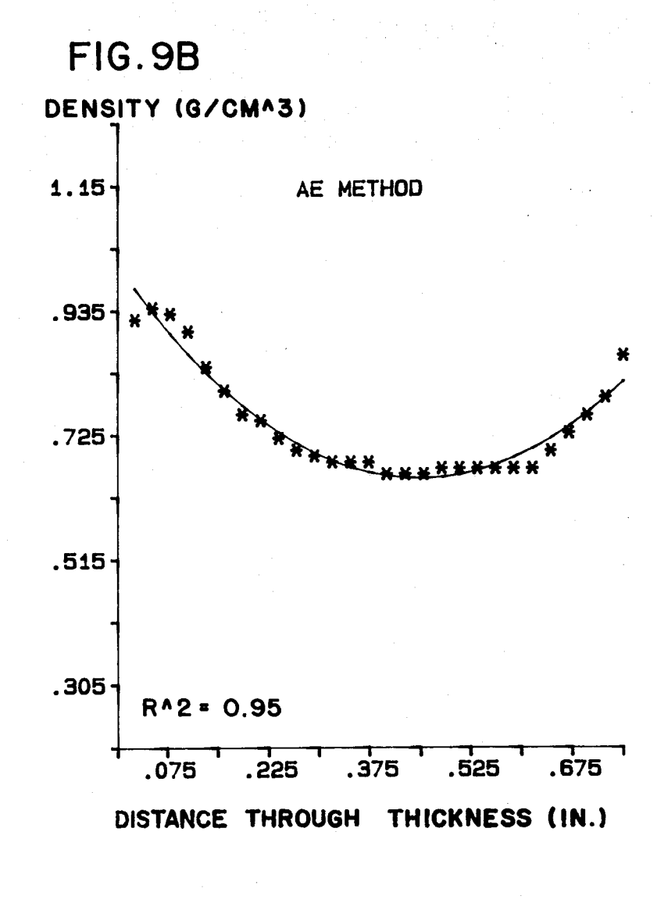

FIG. 9 is a graph of the actual material densities as calculated by using the gravimetric method and the AE method for the high-density particle board sample. Second order polynomial curves were then fitted to the data points obtained from these two methods, such that the squares of the errors were minimized (least squares curve fit). The resulting equations of the form:

$$\text{density} = A \text{ (distance)} + B^2 \text{ (distance)} + C$$

where

Figure 10:
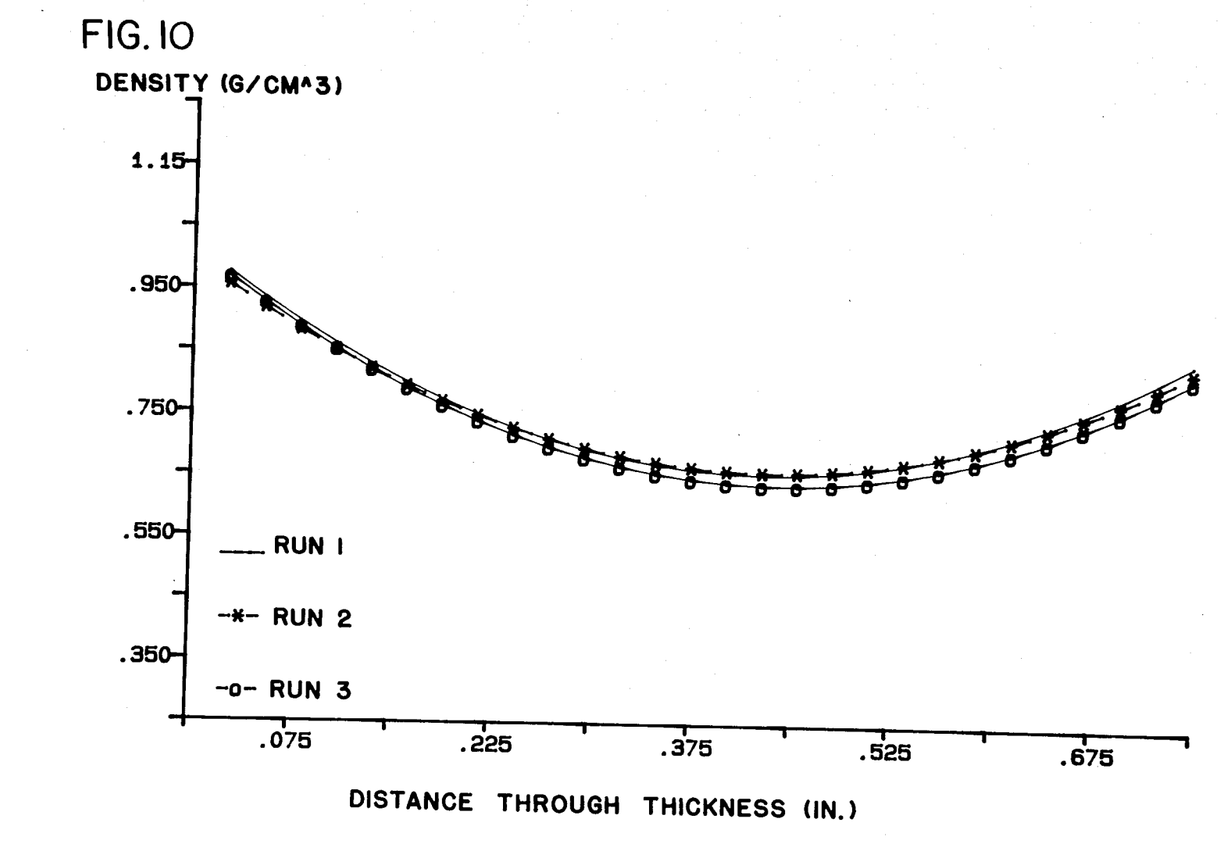
FIG. 10 is a graph of the repeatability of the testing procedure of the invention.

A, B, C = coefficients from least squares fit distance = distance through specimen thickness allow density to be predicted at any point across the thickness of the specimen. The comparisons made in FIG. 10 show the consistency of this density prediction method over three successive data runs using the same particle board sample. The resulting plot shows that such factors as the decreasing sample radius and dulling of the cutting tool were compensated by the calibration technique. By running the calibration material along with the unknown sample, the testing conditions were identical for both samples, and a true comparison could be made. Even if such parameters as depth of cut, output signal gain, or transducer frequency were changed, it is reasonable to assume that the calibration technique would give the same results.

Figure 11A:
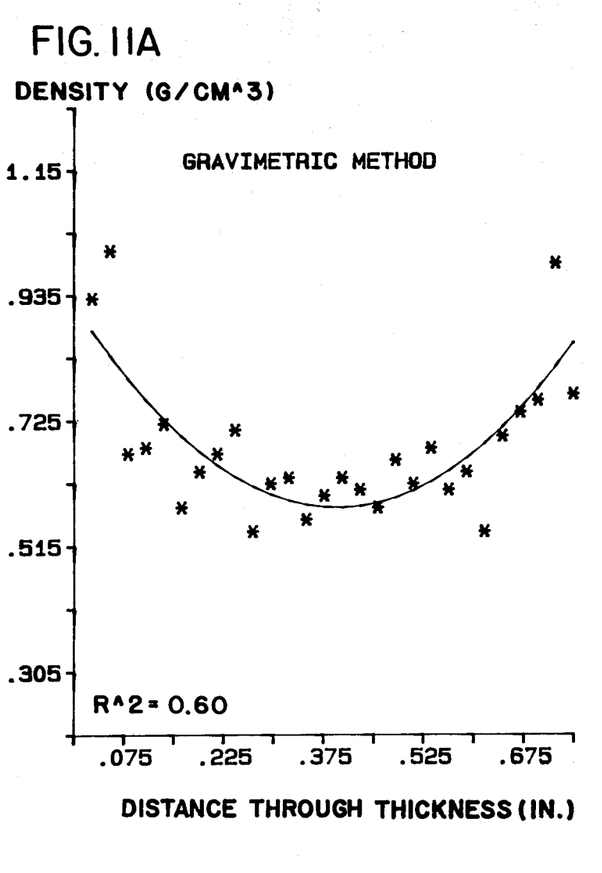
FIG. 11A and 11B hereinafter refered collectively as FIG. 11, is a graph of both gravimetric- and AE-determined density profiles for medium-density particle board.
Figure 11B:
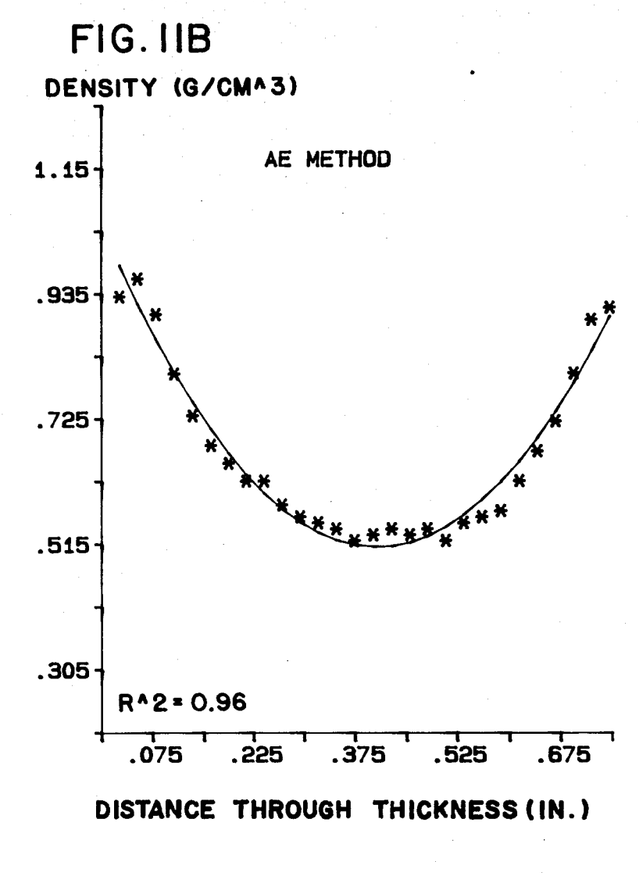
Figure 12:
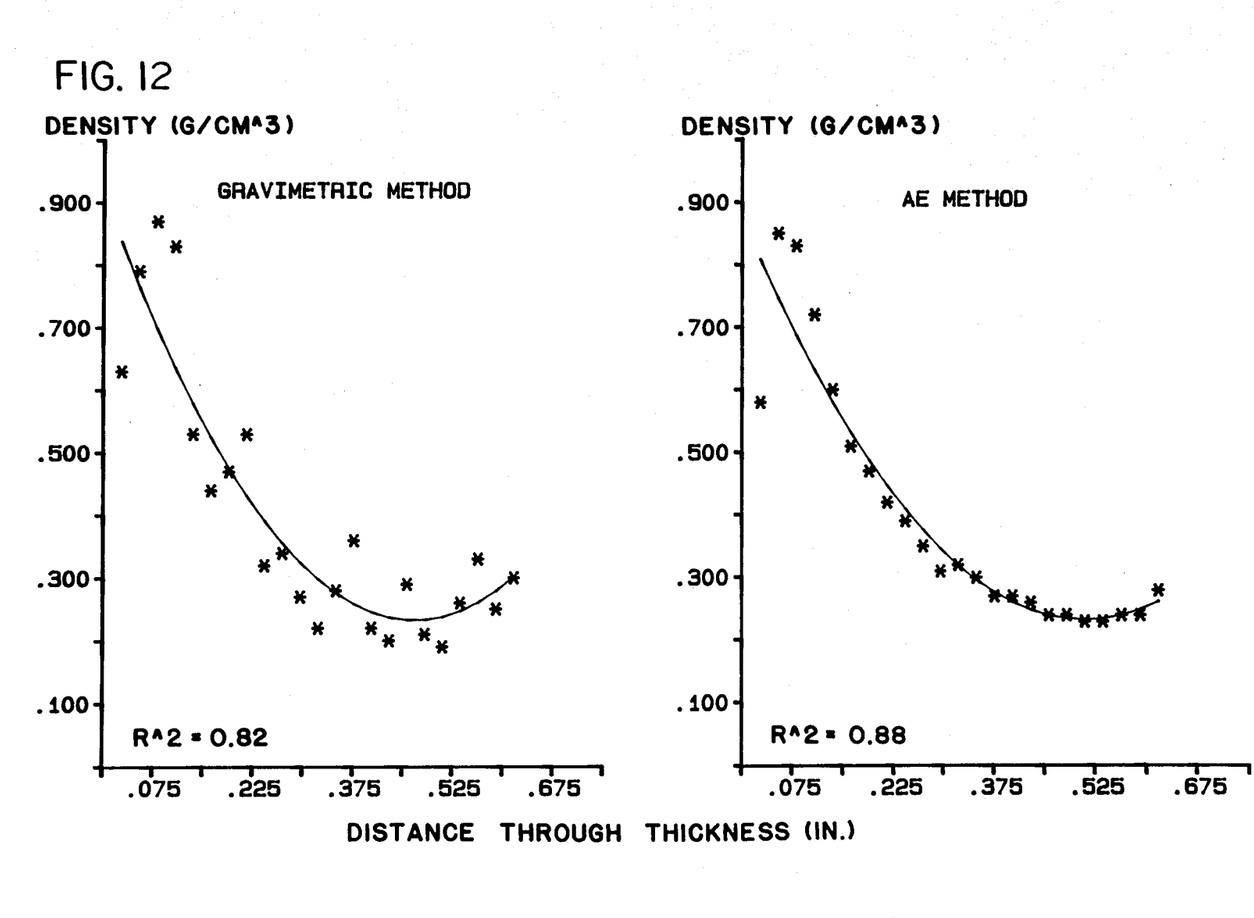
FIG. 12 is a similar graph of gravimetric- and AE-determined density profile for medium-density fiberboard.

FIGS. 11 and 12 show the results of using the same analysis on the medium-density particle board and the medium-density fiberboard, respectively. Once again, the raw data points obtained from both a gravimetric and an AE analysis were fitted with a least squares, second order curve. Although the materials (and therefore the resulting equations) were different than in the previous test of the high-density particle board, reasonable agreement between the AE and gravimetric methods were obtained. The AE technique also appeared much less variable than the gravimetric method.

As mentioned before, it was also noted that as the cutting tool was passed through a sample, some breakout of material occurred toward the end of the run. This would certainly distort the results, and some measures were taken to correct this problem. The breakout was reduced when a sample was tightly secured and supported between two calibration samples. Half of the plot generated from the analysis of the medium-density fiberboard is shown in Fig. 13, the remaining half o the signal was lost due to distortion of the output signal caused by the breakout. Under these circumstances, the bent procedure may be to test the sample by machining in one direction first and then the reverse direction. In this way, the entire profile would be formed by taking half of each run. This problem did not appear with denser boards.

As can be seen from the previous graphs, the source of variability in this study was almost always the gravimetric method. This could be due to the greater sensitivity of the gravimetric method to localized density variation or (as in supported here) to the inaccuracies of the gravimetric method.

As mentioned before, the gravimetric method require a degree of experience on the engine lathe to obtain accurate results. This seems to be verified in Column II on Table 2 (below) where the r$^2$ value increased with specimens that were machined later. It must be pointed out, however, that once the gravimetric data was smoothed out with a 2nd order polynomial regression, a strong correlation existed between RMS and the fitted data (Column IV, Table 2).

TABLE 2

| Material | AE determined density[1] | Gravimetric density[1] | RMS versus Gravimetric density[1] | RMS versus[2] fitted data for gravimetric density method |
|---|---|---|---|---|
| Medium-density fiberboard | 0.88 | 0.32 | 0.48 | 0.88 |
| 45 lb particle board | 0.96 | 0.60 | 0.62 | 0.95 |
| 65 lb particle board | | | | |
| Trial 1 | 0.95 | 0.63 | 0.62 | 0.96 |
| Trial 2 | 0.96 | 0.86 | 0.96 | 0.89 |
| Trial 3 | 0.96 | 0.94 | 1.00 | 0.99 |
| Oriented strand board | 1.00 | .90 | 0.88 | 0.95 |

[1] 2nd order polynomial.
[2] 1st order polynomial.

CONCLUSION

The results from the propsed density measurement technique have shown the method to be extremely repeatable and accurate for use with composite wood materials. Whether specific densities or relative profiles were required, this method offered results quickly and safely with a relatively small amount of instrumentation, compared to the radiation methods. It may also be possible to determine other material characteristics of a composite board, such as modulus of rigidity, using the same analysis techniques.

The repeatability study demonstrated the usefulness of this method when a qualitative evaluation was required. Since the shape of the output signal corresponding to the density profile was maintained over the course of three or more runs, a comparison could be made to a known standard. Also, the resolution was such that any noticeable deviations in shape would correspond to undesirable density characteristics. The 2nd order polynomal regressions yielded a much higher $r^2$ values for the AE predicted densities than the gravimetric method as shown in Table 2. With less variability, a more accurate density reading could be calculated from the magnitude of the output signal. The use of a calibration material helps to eliminate the variability of the equipment and experimental conditions to give consistent results.

The procedure can be used to evaluate full size composite panels in an industrial environment without adversely affecting the finished panel quality.

To those skilled in the art to which this invention relates, many changes in construction and widely differing embodiments and applications of the invention will suggest themselves without departing from the spirit and scope of the invention. The disclosures and the description herein are purely illustrative and are not intended to be in any sense limiting.

What is claimed is:

1. A method of evaluating the density profile of a wood-derived specimen, comprising
   mounting a sample of the wood-derived specimen on a lathe,
   rotating the specimen at high speed,
   coupling a transducer to a cutting tool and bringing the cutting tool into contact with the specimen sample to produce an acoustic emission signal from the wood-derived specimen sample, as the tool is moved across the thickness of the rotating sample,
   transferring the acoustic emission signal into an electric signal,
   amplifying the resultant electrical signal with a first amplifier,
   transmitting the amplified electrical signal to a second amplifier and further amplifying said electrical signal, and
   analyzing said transmitted signal.

2. The method of claim 1 wherein the transducer has a piezoelectric portion.

3. The method of claim 2 wherein said piezoelectric portion is made of lead zirconate titanate.

4. The method of claim 2 wherein said piezoelectric portion is made of quartz.

5. The method of claim 2 wherein said piezoelectric portion is made of polyvinylidene fluoride.

6. A method of evaluating the density profile of a wood-derived specimen, comprising
   mounting a circular sample of the wood-derived specimen on a lathe,
   rotating the specimen at high speed,
   coupling a piezoelectric transducer to a cutting tool and bringing the cutting tool into contact with the specimen to produce an acoustic emission signal from the wood-derived specimen sample, as the tool is moved across the thickness of the rotating sample,
   transferring the acoustic emission signal into an electrical signal,
   amplifying the resultant electrical signal, and
   analyzing said amplified signal.

7. The method of claim 6 wherein said transducer is made of lead zirconate titanate.

8. The method of claim 6 wherein said transducer is made of quartz.

9. The method of claim 6 wherein said transducer is made of polyvinylidene fluoride.

10. Apparatus for evaluating the density profile of a wood-drived specimen, comprising
    a lathe for rotating the specimen at high speed,
    a first transducer coupled to a cutting tool so that the cutting tool can be brought into contact with the specimen to produce an acoustic emission signal from the wood-derived specimen, as the tool is moved across the thickness of the rotating sample,
    transducing means for transferring the acoustic emission signal into an electrical signal,
    an amplifier for amplifying the resultant electrical signal, and
    analysis means for analyzing said amplified signal.

11. The apparatus of claim 10 wherein said transducer is made from lead zirconate titanate.

12. The apparatus of claim 10 wherein said transducer is made from quartz.

13. The apparatus of claim 10 wherein said transducer is made from polyvinylidene flouride.

14. Apparatus for evaluating the density profile of a wood-derived specimen, comprising
    rotating support means for rotating the specimen at high speed,
    a piezoelectric transducer coupled to a cutting tool so that the cutting tool can be into contact with the specimen to produce an acoustic emission signal from the wood-derived specimen, as the tool is moved across the thickness of the rotating sample,
    transfer means for transferring the acoustic emission signal into an electrical signal,
    an amplifier for amplifying the resultant electrical signal, and
    analysis means for analyzing said amplified signal.

* * * * *